United States Patent [19]

Piercey et al.

[11] Patent Number: 5,281,594
[45] Date of Patent: Jan. 25, 1994

[54] SUBSTITUTED 1-(ALKOXYPHENYL)PIPERAZINES WITH ONS AND ANTIHYPERTENSIVE ACTIVITY

[75] Inventors: Montford F. Piercey; William H. Darlington; Arthur G. Romero, all of Kalamazoo, Mich.

[73] Assignee: The Upjohn Company, Kalamazoo, Mich.

[21] Appl. No.: 987,742

[22] Filed: Dec. 9, 1992

Related U.S. Application Data

[63] Continuation of PCT/US91-03943, filed Jun. 10, 1991, which is a continuation of Ser. No. 545,936, Jun. 29, 1990, abandoned.

[51] Int. Cl.$^5$ .................. A61K 31/495; C07D 403/06
[52] U.S. Cl. ..................................... 514/252; 544/370; 548/325.5
[58] Field of Search .......................... 544/370; 514/252

[56] References Cited

U.S. PATENT DOCUMENTS 3,374,237  3/1968  Wright et al. ............... 544/370
5,059,601  10/1991  Salimbeni et al. ............ 544/370

OTHER PUBLICATIONS

P. Critchley et al., Clin. Neuropharmocol. 10:57 (1987).
M. F. Piercey et al., J. Pharmacol. Exp. Ther. 243:391 (1987).
H. Wachtel et al., Life Sci. 32:421 (1983).
W. Kehr Euro. J. Pharmacol. 97:111 (1984).
S. Hjorth et al., Pyschophamacol. 81:89 (1983).
S. Hjorth et al., Life Sci. 28:1225 (1981).
W. E. Hoffmann et al., Neurosci., Abs. 13:908 (1987).
S. Hjorth et al., Naunyn-Schmiedeberg's Arch. Pharmacol. 333:205 (1986).
D. W. Coward et al., J. Pharmacol. Exp. Ther. 252-279 (1990).

*Primary Examiner*—Emily Bernhardt
*Attorney, Agent, or Firm*—Gregory W. Steele; James D. Darnley, Jr.; Martha A. Gammill

[57] ABSTRACT

Substituted 1-(alkoxyphenyl)piperazines are disclosed as partial dopamine agonists useful in the treatment of dopaminergic dysregulation. The compounds 1-[4-[4-(2-methoxyphenyl)-1-piperazinyl]butyl]-3-phenyl-2-imidazolidinone and 1-(3-chlorophenyl)-3-[4-[4-(2-methoxyphenyl)-1-piperazinyl]butyl]-2-imidazolidinone, are preferred in the treatment of Parkinsonism, schizophrenia, and drug addiction.

13 Claims, No Drawings

SUBSTITUTED 1-(ALKOXYPHENYL)PIPERAZINES WITH ONS AND ANTIHYPERTENSIVE ACTIVITY

CROSS REFERENCE TO RELATED APPLICATIONS

This application is a continuation of International Application Serial No. PCT/US91/03943, filed Jun. 10, 1991, which is a continuation of U.S. application Ser. No. 07/545,936, filed Jun. 29, 1990, now abandoned.

FIELD OF THE INVENTION

This invention provides substituted 1-(alkoxyphenyl)-piperazines which are useful in the treatment of conditions evidenced by dopaminergic dysregulation as well as cardiovascular diseases.

BACKGROUND OF THE INVENTION

Dopamine is an important neurotransmitter, important in regulation of human neurological and psychiatric health. Loss of dopaminergic neurons in the substantia nigra pars compacta, located in the brainstem, is responsible for Parkinson's disease, a debilitating neurological disorder of the aged, see O. Horniykiewicz, Fed. Proc., 32:183 (1973). Parkinson's disease is characterized by akinesia (difficulty of initiation of movement) and resting tremor. Because of these properties, it is also referred to as paralysis agitans. This condition is treatable with dopamine agonists. However, because such agonists tend to stimulate dopamine systems too strongly, they induce dyskinesia (excessive abnormal involuntary movements), see T. N. Chase et al., Arch. Neurol. 30:383 (1974).

Dopaminergic dysregulation is also the likely etiology for schizophrenia, perhaps the most serious of all psychiatric disorders see A. Randrup and I. Mukvad, Psychopharmacol. 11:300 (1967) and S. H. S. H. Snyder et al., Science, 184:1234 (1974). Schizophrenia is characterized by clusters of positive and negative symptoms that vary among patients. Positive symptoms include hallucinations, paranoia, feelings of grandiosity, disconnectedness of thought, and a general dissociation from reality. Negative symptoms include withdrawal, flattened affect, and loss of communication. Positive symptoms of schizophrenia are due to excessive activities in dopaminergic neuronal systems. These symptoms are treated with dopamine receptor antagonists, see C. A. Tamminga and J. Gerhlach, "In Psychopharmacology: The Third Generation of Progress", H. Meltzer (ed.), Raven Press, N.Y., 1987, p. 1129. Unfortunately, because such antagonists completely shut off the dopamine system, they induce a variety of symptoms, generally referred to as extrapyramidal symptoms (EPS), which are essentially indistinguishable from natural Parkinsonism, see C. A. Tamminga and J. Gerhlach, "In Psychopharmacology: The Third Generation of Progress", H. Meltzer (ed.), Raven Press, N.Y., 1987, p. 1129. Thus, schizophrenic patients are asked to trade a psychiatric condition for a neurological one. Moreover, dopamine antagonists are generally unable to ameliorate negative symptoms of schizophrenia, probably because these symptoms result from a depression in dopaminergic activity, see R. J. Wyatt, Research in the Schizophrenic Disorders: The Stanley R. Dean Award Lectures", vol. 2, R. Cancro and S. R. Dean (eds), Spectrum Publ., 1985, p. 225.

A different approach to treating diseases of dopaminergic dysregulation is through dopamine partial agonists. Such agents are dopamine agonists but their maximal effects are weaker than full dopamine agonists such as apomorphine and dopamine itself. Such agents will act as agonists in systems having little or no dopaminergic activity, and as antagonists when dopaminergic activity is high. Thus, such agents could treat both positive and negative symptoms of schizophernia, as well as Parkinson's disease. The concept of partial agonists is not specific to dopaminergic systems, and the theoretical basis for the concept is discussed in detail elsewhere see E. J. Ariens, Molecular Pharmacology, vol. 1, Academic Press, N.Y., pp. 503 (1964). Partial agonist activity is defined by the level of intrinsic activity. Intrinsic activities are defined as the maximal effect of a drug expressed as a fraction of the maximal effects of the most effective agonists. Dopamine antagonists have intrinsic activities of zero. That is, they have no agonist effects, but they bind to dopamine receptors, thus blocking access of dopamine and other dopamine agonists to activate the receptors. On the other hand, Full dopamine agonists have intrinsic activities of one; at their highest concentrations they stimulate dopaminergic systems to express their maximal possible outputs. Partial agonists have intrinsic activities between zero and one. Partial agonists by themselves will stimulate dopaminergic systems, but even at their highest dosage they cannot stimulate these systems to produce their maximal possible outputs. Since at their highest doses they will fully saturate the receptor sites, they block access of full agonists (e.g. dopamine) and, therefore, act as antagonists.

Since the full expression of biological activity is equal to the product of the percentage of receptors occupied times the intrinsic activity of the occupying drug, one should be able to "clamp" dopaminergic systems in a normal range by saturating the receptors with a drug having an intrinsic activity near the normal fraction of receptors occupied by dopamine, the natural mediator. Since the fraction of receptors normally occupied is not known, the ideal intrinsic activity for a partial agonist is also not known. This is accentuated by the fact that few dopamine partial agonists are known. The current invention describes certain phenylureas of sufficiently low intrinsic activity to be useful as partial dopamine agonists for the treatment of disease conditions resulting from or worsened by dysregulation of dopaminergic systems. Such conditions include schizophrenia and Parkinsonism, and may also include such diseases as drug addiction, attention deficit disorders (ADD), Tourrette's syndrome, autism, appetite control, hyperprolactinemia and other endocrine disorders, sexual dysfunction, and cardiovascular disorders such as hypertension and congestive heart failure.

INFORMATION DISCLOSURE

The compounds of the invention are generally disclosed in U.S. Pat. No. 3,374,237 (Wright et al.) and are said to be useful as tranquilizers. However, neither the dopamine agonist nor antagonist activities of the present invention are taught therein.

A number of known compounds are said to be useful as dopamine partial agonists. These include:

The lisuride derivative 1-1-diethyl-3-(6-methyl-8α-ergoline)-urea dihydrogenphosphate (also known as transdihydrolisuride or (TDHL)), as disclosed in P. Critchley and D. Parkes, Clin. Neuropharmocol. 10:57

(1987), M. F. Piercey et al., J. Pharmacol. Exp. Ther. 243:391 (1987), H. Wachtel and R. Dorow, Life Sci. 32:421 (1983), and W. Kehr, Euro. J. Pharmacol. 97:111 (1984);

The phenylpiperidine (−)-3-(3-hydroxyphenyl)-N-n-propylpiperidine ((−)-3-PPP), as disclosed in S. Hjorth et al., Pyschophamacol. 81:89 (1983), S. Hjorth et al., Life Sci. 28:1225 (1981), and W. E. Hoffmann and M. F. Piercey, Neurosci, Abs. 13:908 (1987);

7-hydroxy-1,2,3,4,4a,5,6,10-octahydrobenzo(f)quinoline (HW-165), as disclosed in W. E. Hoffmann and M. F. Piercey, Neurosci, Abs. 13:908 (1987), and S. Hjorth et al., NaunynSchmiedeberg's Arch. Pharmacol. 333:205 (1986);

The aminoergolines N-[(8-α)-2,6-dimethyl-ergoline-8-yl]-2,2-dimethylpropanamide (SDZ 208-911) and N-[(8-α)-2-chloro-6-methyl-ergoline-8-yl]-2,2-dimethylpropanamide (SDZ 208-912) as disclosed in D. W. Coward et al., J. Pharmacol. Exp. Ther. 252:279 (1990).

However, none of these references teach or suggest the substituted 1-(alkoxyphenyl)piperzines of the present invention.

SUMMARY OF THE INVENTION

This invention provides substituted 1-(alkoxyphenyl)-piperazines of formula I wherein X is hydrogen or Cl;

$R_1$ and $R_2$ are the same or different and are selected from the group consisting of hydrogen, methoxy, or ethoxy, provided that only one of $R_1$ or $R_2$ is hydrogen; or a pharmacologically acceptable salt thereof.

More particularly, this invention provides the compound 1-(3-chlorophenyl)-3-[4-[4-(2-methoxyphenyl)-1-piperazinyl]butyl]-2-imidazolidinone and, most particularly, the compound 1-[4-[4-(2-methoxyphenyl)-1-piperazinyl]butyl]-3-phenyl-2-imidazolidinone.

The invention also relates to the use of the compounds of Formula I or their pharmacologically acceptable salts for the preparation of pharmaceutical formulations.

More particularly, the invention provides a pharmaceutical composition comprising the compound 1-(3-chlorophenyl)-3-[4-[4-(2-methoxyphenyl)-1-piperazinyl]butyl]-2-imidazolidinone and, most particularly, the compound 1-[4-[4-(2-methoxyphenyl)-1-piperazinyl]butyl]-3-phenyl-2-imidazolidinone and a pharmaceutically acceptable carrier.

This invention also provides a method of treating humans with an effective amount of a compound of the invention to treat dopaminergic system disease. More particularly, this invention provides a method of treating humans with a compound of the invention to relieve symptoms of Parkinsonism, schizophrenia, and drug abuse.

Most particularly, this invention provides a method of treating Parkinsonism, schizophrenia, and drug abuse with the compound 1-[4-[4-(2-methoxyphenyl)-1-piperazinyl]butyl]-3-phenyl-2-imidazolidinone or 1-(3-chlorophenyl)-3-[4-[4-(2-methoxyphenyl)-1-piperazinyl]butyl]-2-imidazolidinone.

DETAILED DESCRIPTION OF THE INVENTION

The particular compounds of Formula I wherein X is hydrogen or Cl, $R_1$ is methoxy, and $R_2$ is hydrogen are preferred; the compound wherein X is hydrogen is most preferred. Examples of pharmacologically acceptable salts include hydrochloride, hydrobromide, fumarate, maleate, succinate, citrate, tosylate, and mesylate.

When used as a pharmaceutical formulation, it is possible to modify the compounds into forms suitable for administration. In this case, at least one compound of Formula I and/or one of its pharmacologically acceptable salts are mixed or combined with at least one carrier. Carriers include inorganic or organic substances which are suitable for enteral, parenteral, or topical administration and which do not react with the new compounds. Examples of suitable vehicles include water, vegetable oils, benzyl alcohols, polyethylene glycols, gelatine, carbohydrates, such as lactose or starch, magnesium stearate, talc, and vaseline. In particular, tablets, coated tablets, capsules, syrups, liquids, drops, or suppositories are used for enteral applications, for parenteral administration solutions of an oily or aqueous nature are preferred, but suspensions, emulsions, or implants are used as well. Ointments, creams, or powders are used for topical administration. It is also possible to sterilize and/or lyophilize these compounds for subsequent use in the preparation of products.

The formulations may also contain one or more pharmacologically acceptable auxiliaries, such as lubricants, preservatives, stabilizers, wetting agents, emulsifiers, salts, buffers, colorants, flavorings, and aromatic substances.

The invention also relates to the use of the compounds of formula I or their pharmacologically acceptable salts for the therapeutic treatment of a human and for the control of diseases of the dopaminergic system, particularly schizophrenia, Parkinsonism, and drug addiction, especially cocaine base. While not wishing to be bound by any theory, the compounds of the invention will treat both positive and negative symptoms of schizophrenia, since these compounds are both dopaminergic agonists and antagonists. As they do not completely inhibit the dopamingeric system they do not induce chemical Parkinsonism. On the contrary, these compounds are useful for treating Parkinsonism because of their dopaminergic agonist effects and low intrinsic activities which do not induce dyskinesia. Further, the effect of licit and illicit drugs on the dopaminergic system may be a factor leading to drug addiction; among the various physiological effects of cocaine, for instance, is the release of dopamine. However, chemical therapy for drug abuse has been largely unsuccessful. Thus, because of their dopaminergic effects the compounds of the invention are useful in the treatment of drug addiction. Other disorders in which regulation of the dopaminergic system may play a role include attention deficit disorders, Tourette's syndrome, autism, and appetite control. The compounds can also be used in endocrine disorders, for example hyperprolactemia, and cardiovascular disorders such as hypertension and congestive heart failure.

As a general rule the compounds, when used as a medicament, are administered in doses similar to known and commercially available products, such as the dopaminergic agents TDHL, bromocriptine, and haloperidol. The preferred method of administration is oral. The preferred dose is between 0.2 and 500 mg., in particular between 0.2 and 50 mg. per dose. The preferred daily dose is between about 0.001 and 10 mg./kg. body weight. However, the specific dose for a patient depends on a wide variety of factors, for example on the efficacy of the specific compound employed (alone or when used in combination with other medicaments), the severity of the disorder for which therapy is sought, on the age, weight, health, sex, and diet of the patient, on the method of administration, and on the excretion rate.

By following the preceding description, and without further elaboration, one skilled in the art can utilize the present invention to the fullest extent. The following examples are illustrative only and not limiting of the remaining disclosure. In preparative methods, all starting materials are known and/or are commercially available or are readily prepared from known starting materials. In the examples, unless otherwise indicated, all temperatures are given in degrees Celsius, parts and percentages are by weight, and mass spectroscopy data are given in mass per charge.

SYNTHESIS OF REPRESENTATIVE COMPOUNDS

Example 1

1-[4-[4-(2-methoxyphenyl)-1-piperazinyl]butyl]-3-phenyl-2-imidazolidinone a) Preparation of 1-phenyl-3-(4-chlorobutyl)-2-imidazolidone A mixture of 1-phenyl-2-imidazolidone (3.24 g, '20.0 mmol), 1-bromo-4-chlorobutane (10.29 g, 60.0 mmol), tetrabutylammonium bromide (0.64 g, 2.0 mmol), 50% aqueous sodium hydroxide (60 mls), and toluene (100 ml) is stirred in an oil bath maintained at 60° C. for 9 hours. The reaction mixture is diluted with water and extracted twice with diethylether. The combined extracts are washed with brine and dried (magnesium sulfate). The solvent is removed in vacuo to leave a light-yellow oil (9.2 g). Purification by flash chromatography (silicon dioxide, 230–400 mesh; 3:1 hexane/ethyl acetate) gives a colorless solid (4.83 g). A sample (0.50 g) is crystallized from diethylether/hexane to give colorless crystals (1-phenyl-3-(4-chlorobutyl)-2-imidazolidone; 0.49 g, mp 47.5°–49° C.).

b) Preparation of 1-[4-[4-(2-methoxyphenyl)-1-piperazinyl]butyl]-3-phenyl-2-imidazolidinone A mixture of 1-phenyl-3-(4-chlorobutyl)-2-imidazolidone (4.00 g, 15.8 mmol)(from Example 1(a)), 1-(2-methoxyphenyl)piperazine (4.62 g, 24.0 mmol), and sodium carbonate (3.40 g, 32.0 mmol) in n-butanol (40 ml) is stirred in an oil bath maintained at 140° C. for 17 hours. The solvent is removed in vacuo, the residue is diluted with water, and the mixture is extracted with 3:1 diethylether/tetrahydrofuran. The ether solution is washed twice with water and once with brine. The solution is dried, and the solvent is removed in vacuo to leave an oil (7.81 g). Crystallization from diethylether/hexane and recrystallization from ethyl acetate/hexane gives white crystals (1-[4-[4-(2-methoxyphenyl)-1-piperazinyl]butyl]-3-phenyl-2-imidazolidinone; 4.32 g, 86%; mp 94°–95° C.). Mass spec. m+ at m/z 408.

Exact Mass Calcd. for $C_{24}H_{32}N_4O_2$: 408.2525: Found: 408.2527.

Anal. Calcd: C, 70.56; H, 7.90; N, 13.71. Found: C, 70.66; H, 7.83; N, 13.93.

Example 2

1-(3-chlorophenyl)-3-[4-[4-(2-methoxyphenyl)-1-piperazinyl]butyl]-2-imidazolidinone a) Preparation of 1-(3-chlorophenyl)-3-(4-chlorobutyl)-2-imidazolidone.

A mixture of 1-(3-chlorophenyl)-2-imidazolidone (5.92 g, 30.0 mmol), 1-bromo-4-chlorobutane (10.29 g, 60.0 mmol), tetrabutylammonium bromide (0.97 g, 3.0 mmol), 50% aqueous sodium hydroxide (90 ml), and toluene (150 ml) is stirred in an oil bath maintained at 60° C. for 10 hours. The reaction mixture is diluted with water and extracted with methylene chloride. The combined extracts are washed with brine and dried (magnesium sulfate). The solvent is removed in vacuo to leave a yellow oil (12.34 g). Purification by flash chromatography (silicon dioxide, 230–400 mesh; 3:1 hexane/ethyl acetate) gives a yellow oil (1-3-chlorophenyl)-3-(4-chlorobutyl)-2-imidazolidone; 8.22 g). Mass spec. m+ at m/z 286, 288. Some of the corresponding bromide is also evident at m/z 330, 332.

Exact Mass Calcd. for $C_{13}H_{16}Cl_2N_2O$: 286.0640: Found: 286.0629.

b) Preparation of 1-(3-chlorophenyl)-3-[4-[4-(2-methoxyphenyl)-1-piperazinyl]butyl]-2-imidazolidinone.

A mixture of 1-(3-chlorophenyl)-3-(4-chlorobutyl)-2-imidazolidone (4.54 g, 15.8 mmol)(from Example 2(a)), 1-(2-methoxyphenyl)piperazine (4.62 g, 24.0 mmol), and sodium carbonate (3.40 g, 32.0 mmol) in n-butanol (40 ml) is stirred at reflux for 18 hours. The solvent is removed in vacuo, the residue is diluted with water, and the mixture is extracted with 1:1 diethylether/tetrahydrofuran. The ether solution is washed twice with water and once with brine, and the solvent is removed in vacuo to leave a solid (8.18 g). Crystallization from ethyl acetate/hexane gives white crystals (4.90 g). A sample (2.35 g) is recrystallized from ethyl acetate/hexane to give a white solid (1-(3-chlorophenyl)-3-[4-[4-(2-methoxyphenyl)-1-piperazinyl]butyl]-2-imidazolidinone, 2.11 g, mp 87°–89° C.). Mass spec. m+ at m/z 442.

Exact Mass Calcd. for $C_{24}H_{31}{}^{35}ClN_4O_2$: 442.2135; Found: 442.2148.

Anal. Calcd.: C, 65.07; H, 7.05; N, 12.65; Cl, 8.00. Found: C, 64.96; H, 7.33; N, 12.64; Cl, 8.02.

In an analogous manner, the remaining compounds of the invention are synthesized using the same or similar molar ratios, under the same or similar reaction and purification conditions. For example, 1-phenyl-3-(4-chlorobutyl)-2-imidazolidone (the product of Example 1(a)) is combined with 1-(3-methoxyphenyl)piperazine to form 1-[4-[4-(3-methoxyphenyl)-1-piperazinyl]butyl]-3-phenyl-2-imidazolidinone, 1-[4-[4-(2-ethoxyphenyl)-1-piperazinyl]butyl]-3-phenyl-2-imidazolidinone is made by combining the product of Example 1(a) with 1-(2-ethoxyphenyl)piperazine, and 1-[4-[4-(3-ethoxyphenyl)-1-piperazinyl]butyl]-3-phenyl-2-imidazolidinone is made by combining the product of Example 1(a) with 1-(3-ethoxyphenyl)-piperazine. In a similar manner, 1-(3-chlorophenyl)-3-(4-chlorobutyl)-2-imidazolidone (the product of Example 2(a)) is combined with 1-(3-methoxyphenyl)piperazine to form 1-(3-chlorophenyl)-3-[4-[4-(3-methoxyphenyl)-1-piperazinyl]butyl]-2-imidazolidinone, 1-(3-chlorophenyl)-3-[4-[4-(2-ethoxyphenyl)-1-piperazinyl]butyl]-2-imidazolidinone is made by combining the product of Example 2(a) with 1-(2-ethoxyphenyl)piperazine, and 1-(3-chlorophenyl)-3-[4-[4-(3-ethoxyphenyl)-1-piperazinyl]butyl]-2-imidazolidinone is made by combining the product of Example 2(a) with 1-(3-ethoxyphenyl)piperazine. Where appropriate, one skilled in the art will recognize the compounds for which reaction ratios or conditions are altered. In such a case, the reaction may be successfully carried to completion using conventional modifications known by those skilled in the art.

Biological Screens

The compounds of the invention are tested in a series of assays known by those skilled in the art as predictive for activity as dopamine partial agonists. A series of structurally similar prior art compounds, as disclosed in U.S. Pat. No. 3,374,237 (Wright et al), are also screened in two tests indicative of their use as agonists or antagonists. The following compounds are synthesized following the procedure described in the Wright, et al patent: 1-(m-chlorophenyl)-3-[3-[4-(p-methoxy-phenyl)-1-piperazinyl]propyl]-2-imidazolidinone (Example 11); 1-(m-chlorophenyl)-3-[3-[4-(m-tolyl)-1-piperazinyl]-propyl]-2-imidazolidinone (Example 14); and 1-phenyl-3-[3-(4-phenyl-1-piperazinyl)propyl]-2-imidazolidinone hydrochloride (Example 17). Drugs. The drug standards used in these studies, and their source are: TDHL, Schering AG, Berlin, F.R.G.; (−)-3-PPP and HW-165, Prof. Arvid Carlsson, Department of Pharmacology, University of Göteborg, Göteberg, Sweden; and SDZ 208-911 and -912, Sandoz Ltd., Basle, Sweden. Except as otherwise stated, all other chemicals are widely available from commercial sources.

1. Dopamine Receptor Binding

Since a dopamine partial agonist must bind to the dopamine receptor, binding studies are used to determine the affinity of a compound for the receptor. The benzamide raclopride is reported to be a selective ligand for the D2 receptor based upon binding studies conducted in vivo and in vitro, see C. Kohler et al, "Specific In Vitro and In Vivo Binding of $^3$H-Raclopride", Biochem. Pharmacol. 34:2251–2259 (1985). PET scanning in humans has confirmed that raclopride binds to the D2 receptor. L. Farde, et al, "Substituted Benzamides as Ligands for the Visualization of Dopamine Receptors Binding in the Human Brain by Positron Emission Tomography" PNAS 82:3863–3867 (1985). The dopamine receptor affinity of the prior art compounds is compared to two compounds of the present invention following the procedure described in R. H. Roth. Comm. Pyschopharm., 3:429 (1979), with the exception that a Cambridge cell harvester is used for sample filtration. $^3$H-Raclopride is obtained from New England Nuclear with a specific activity of 83.4 Ci/nmole. Studies by Kohler demonstrated that raclopride has a Kd of about 1.2 nM and a B max equal to 23.5 pmoles/g tissue in rat striata. Using whole rat brain we find a Kd of 1.24 nM and Bmax of 1.6 pmoles/g tissue. Compounds are tested at least four concentrations in triplicate. Non-specific binding is determined using 1 uM thioridazine. Generally the total ligand bound is about 1.5% of that added, and specific binding is 93% of the total bound. Variation between samples is approximately 6.0%. Results are expressed in Ki (=the amount of a compound required to bind fifty percent (50%) of the receptors). Referring to Table 1, Examples 1 and 2 bind to dopamine receptors with extremely high affinity, having Ki of 2.6 and 3.7 nM, respectively. In contrast, the closest prior art compounds have little affinity for the receptors. Thus, 1-phenyl-3-[3-(4-phenyl-1-piperazinyl)propyl]-2-imidazolidinone has a Ki of 323 nM, whereas 1-(m-chlorophenyl)-3-[3-[4-(m-tolyl)-1-piperazinyl]propyl]-2-imidazolidinone and 1-(m-chlorophenyl)-3-[3-[4-(p-methoxy-p-henyl)-1-piperazinyl]-propyl]-2-imidazolidinone do not bind at all, even at concentrations as high as 1,000 nM and 10,000 nM, respectively.

In comparison, other known dopamine agonists and partial agonists show activity in the range of 0.47 to 177 nM. These results are also shown in Table 1.

2. Cage Climbing

Apomorphine is a known full dopamine agonist. Administration to mice stimulates dopaminergic receptors which results in enhanced locomotor activity, including climbing up the sides of wire cages. Antagonism of apomorphine-induced abnormal behavior is a direct expression of the blockade of the dopamine receptor within the central nervous system. See Haase and Janssen, "The Action of Neuroleptic Drugs", Elsevier, Amsterdam, 1985, pp. 301. As a specific measure of their antagonistic effect, both the prior art compounds and the compounds of the invention are tested in their ability to block agonist-induced locomotor activity. In this procedure, a group of 4 CF-1 mice (18–22 gm each) are injected i.p. with the test compound prepared in 0.25% methylcellulose. After 25 minutes, the animals are injected with apomorphine hydrochloride at 2.5 mg/kg i.p. Each group of 4 mice is then placed on the floor of a wire cage (5"×5"×12") and observed for 5–10 minutes after apomorphine injection for a measure of "cage climbing". During this time, mice that climb the walls more than half-way to the top (6") are removed from the cage. A compound is considered an antagonist of apomorphine if 2 or more mice remain in the cage at the end of 10 minutes. Active compounds are retested at dose levels decreasing in 0.3 or 0.5 log intervals and the number of mice remaining in the cage is used as a quantal response metameter to calculate the ED$_{50}$ as Spearman and Karber, Finney, D. J., Statistical Methods in Biological Assay, Hafner Publ. Co., New York, N.Y., p. 524, 1952. As can be seen, the prior art compounds have no effect on apomorphine-induced climbing behavior, while Examples 1 and 2 reversed the effect at 12 and 42 mg/kg, respectively.

As the prior art compounds show neither agonistic nor antagonistic effects in model systems, no further testing was pursued.

3. Dopamine Nerve Impulse Generation

Dopaminergic agonists, such as apomorphine, depress nerve impulses generated by dopaminergic neurons. Indeed, all full dopamine agonists can completely suppress impulse generation so that the dopamine cells stop firing completely. As the name implies, partial agonists depress impulse generation only partly. In contrast to the effects of dopamine full and partial agonists, dopamine antagonists either do not effect nerve impulse activity of dopamine neurons or increase them.

Dopamine partial agonists act as dopamine antagonists when dopaminergic activity is excessive. Excessive dopaminergic activity can be induced by amphetamine, which causes dopamine to be released at nerve terminals in dopaminergic postsynaptic areas such as the caudate nucleus. This released dopamine activates negative feedback systems connecting postsynaptic dopaminergic areas to dopamine cells (e.g., the caudate nucleus feeds back onto substantia nigra neurons). Through this negative feedback system, amphetamine inhibits nerve impulses in dopamine neurons. Because dopamine antagonists block the access of of dopamine to its receptors, these agents block the activation of the negative feedback pathways. Thus, dopamine antagonists and dopamine partial agonists block or reverse amphetamine's depression in dopamine nerve impulse activity. Because dopamine antagonists block not only the dopamine released by amphetamine but also the dopamine released for maintenance of a normal physiological state, dopamine antagonists not only completely reverse the effects of amphetamine but may actually cause an increase in dopamine neuron impulse activity (i.e. reverse amphetamine's inhibition by more than 100%). In contrast, partial agonists reverse the effects of amphetamine, but do not increase impulse activity above normal. Indeed, partial agonists with higher intrinsic activities only partially reverse the effects of amphetamine.

The activity of two compounds of the invention are compared with other known drugs in their effect on nerve impulse generation. Sprague-Dawley rats weighing between 250-350 g are anesthetized with chloral hydrate (400 mg/kg i.p.). Supplemental doses (50-100 mg/kg) are administered as needed. The fermoral artery and vein are cannulated to measure blood pressure and to permit i.v. administration of drug. Body temperature is maintained at 37° C. using a deltaphase isothermal pad. The animal's head is held in a stereotaxic device and a small burr hole made in the cranium. Extracellular action potentials are recorded with a glass microelectrode (tip size<1μm) filled with pontamine sky blue dye in 2M sodium chloride.

Dopaminergic neurons are identified by their long duration action potential (>2.5 ms), shape and firing pattern (>12 spikes/s) according to B. S. Bunney and G. K. Aghajanian "Antipsychotic Drugs and Central Dopaminergic Neurons: A Model for Predicting Therapeutic Efficacy and Incidence of Extrapyramidal Side Effects, In: Predictability in Psychopharmacology: Preclinical and Clinical Correlates, eds.", Raven Press, N.Y., pp. 225-245 (1975). The recording electrode is hydraulically lowered into the substantia nigra (SNPC), an area of dopamine neurons, (P5.0-6.0 mm, L2.0-2.2 mm, v7.0-8.0 mm) according to the coordinates of G. Paxinos and C. Watson "The Rat Brain in Stereotaxic Coordinates", Academic Press, Sydney (1982).

At the termination of each recording session, the location of the cell in the substantia nigra is identified by passing 10 μA cathodic current through the recording electrode for 10-20 minutes. The brain is then removed, fixed in 10% formalin, sectioned and stained, and the pontamine sky blue deposit verified in each animal.

All drug solutions are made in distilled water. Each drug injection contained no more than 0.15 ml of a given concentration, followed by a 0.2-0.4 ml of physiological saline to clean the catheter of any residual drug. Drug effects are measured as changes in firing rates as indicated by an integrated output throughout the experiment.

Neither 1-[4-[4-(2-methoxyphenyl)-1-piperazinyl]butyl]-3-phenyl-2-imidazolidinone nor 1-(3-chlorophenyl)-3-[4-[4-(2-methoxyphenyl)-1-piperazinyl]butyl]-2-imidazolidinone completely depressed SNPC cells, but rather behaved as dopamine partial agonists. The maximal depression of 1-[4-[4-(2-methoxyphenyl)-1-piperazinyl]butyl]-3-phenyl-2-imidazolidinone on DA cell firing is 32% of control at 1 mg/kg i.v., whereas that for 1-(3-chlorophenyl)-3-[4-[4-(2-methoxyphenyl)-1-piperazinyl]butyl]-2-imidazolidinone is 54% of control at 1 mg/kg i.v. Increasing the dose of 1-(3-chlorophenyl)-3-[4-[4-(2-methoxyphenyl)-1-piperazinyl]butyl]-2-imidazolidinone to 3 mg/kg does not further increase the depression in SNPC cells. The dose required to attain 50% of maximal effect is 16±8 μg/kg (n=7) for 1-[4-[4-(2-methoxyphenyl)-1-piperazinyl]butyl]-3-phenyl-2-imidazolidinone and 108±68 μg/kg (n=6) for 1-(3-chlorophenyl)-3-[4-[4-(2-methoxyphenyl)-1-piperazinyl]butyl]-2-imidazolidinone.

Finally, in this system, 1-[4-[4-(2-methoxyphenyl)-1-piperazinyl]butyl]-3-phenyl-2-imidazolidinone antagonized excessive dopaminergic activity induced by amphetamine. Consistent with its partial agonist effects, it only partially antagonized amphetamine (Table 3).

4. Behavioral Effects

Amphetamine releases excessive dopamine and induces a state in animals that serves as a model of positive-symptom schizophrenia. Amphetamine stimulates excessive locomotor activity in the rat, including uncontrolled stereotyped movements, characterized by licking and chewing. This model is indicative of the human response as amphetamine abuse is characterized by schizophrenic-like behavior in humans. Thus compounds may be tested in their ability to antagonize amphetamine.

In addition to antagonizing stereotypical movements, haloperidol, a standard dopamine antagonist antipsychotic, induces catalepsy at doses similar to those required to antagonize amphetamine. Thus the range of effectiveness is very narrow. It is believed that induction of catalepsy is a predictor of EPS side effects at therapeutic doses.

As a screen for antagonism of amphetamine-induced stereotyped behavior, we employed the following methods. Sprague-Dawley rats are injected s.c. with either 3 mg/kg of apomorphine or 10 mg/kg of d-amphetamine. The animals are then observed for 30 minutes for licking and chewing. A score of 0-2 is given every 5 minutes, yielding a possible maximum of 12. Drugs tested as antagonists are injected i.p. 30 minutes before amphetamine. A control group receiving only the dopamine agonists are always tested in parallel for statistical evaluation. Results are expressed as the threshold dose required to induce the behavior observed and are compiled in Table 4.

Example 1 antagonizes amphetamine stereotypy with a potency greater than that of halperidol but produces catalepsy only at doses much higher that required to block amphetamine-induced stereotypy. Thus, consistent with its action as a dopamine partial agonist, Example 1 is not likely to produce EPS at therapeutic doses.

TABLE 1

| DOPAMINE RECEPTOR BINDING | |
|---|---|
| | Ki (nM)[1] |
| 1-[4-[4-(2-methoxyphenyl)-1-piperazinyl]butyl]-3-phenyl-2-imidazolidinone (Example 1) | 2.6 |
| 1-(3-chlorophenyl)-3-[4-[4-(2-methoxyphenyl)-1-piperazinyl]butyl]-2-imidazolidinone (Example 2) | 3.7 |
| 1-phenyl-3-[3-(4-phenyl-1-piperazinyl)propyl]-2-imidazolidinone | 323 |
| 1-(m-chlorophenyl)-3-[3-[4-(m-tolyl)-1-piperazinyl]propyl]-2-imidazolidinone | i.a. at 1,000 |
| 1-(m-chlorophenyl)-3-[3-[4-(p-methoxyphenyl)-1-piperazinyl]propyl]-2-imidazolidinone | i.a. at 10,000 |
| Haloperidol | 1.8 |
| Apomorphine | 177 |
| SDZ 208-911 | 0.74 |
| SDZ 208-912 | 15.7 |
| (−)-z-(dipropylamino)-2,3-dihydro-1-H-phenalen-5-ol | 0.47 |
| TDHL | 0.95 |

[1]Dose for 50% occupation.
i.a. = Inactive at specified concentration.

TABLE 2

BLOCK OF APOMORPHINE CAGE CLIMBING

| | $ED_{50}$[1] |
|---|---|
| 1-[4-[4-(2-methoxyphenyl)-1-piperazinyl]-butyl]-3-phenyl-2-imidazolidinone (Example 1) | 12 |
| 1-(3-chlorophenyl)-3-[4-[4-(2-methoxyphenyl)-1-piperazinylbutyl]-2-imidazolidinone (Example 2) | 42 |
| 1-(m-chlorophenyl)-3-[3-[4-(p-methoxyphenyl)-1-piperazinyl]propyl]-2-imidazolidinone | i.a. |
| 1-phenyl-3-[3-(4-phenyl-1-piperazinyl)-propyl]-2-imidazolidinone | i.a. |
| 1-(m-chlorophenyl)-3-[3-[4-(m-tolyl)-1-piperazinyl]propyl]-2-imidazolidinone | i.a. |
| TDHL | 35 |
| Clozapine | 6 |

[1]Dose (mg/kg) for elimination of behavior in 2 of 4 animals.
i.a. = Inactive at top dose of 50 mg/kg.

TABLE 3

| | Agonist | | Antagonist | |
|---|---|---|---|---|
| | $ED_{50}$[1] | Max.[2] | $ED_{50}$[3] | Max.[4] |
| Apomorphine | 10 | 100% | i.a. | 0% |
| HW-165 | 180 | 85% | n.t. | |
| (−)-3-PPP | 86 | 70% | n.t. | |
| TDHL | 21 | 53% | 136 | 60% |
| 1-(3-chlorophenyl)-3-[4-[4-(2-methoxyphenyl)-1-piperazinyl]butyl]-2-imidazolidinone (Example 2) | 108 | 54% | 343 | 73% |
| 1-[4-[4-(2-methoxyphenyl)-1-piperazinyl]butyl]-3-phenyl-2-imidazolidinone (Example 1) | 16 | 36% | 40 | 70% |
| SDZ 208-911 | 38 | 38% | 132 | 92% |
| SDZ 209-912 | 21 | 16% | 115 | 93% |
| Haloperidol | i.a. | 0% | 8 | 163% |

[1]Dose (μg/kg) to depress firing by 50%.
[2]Maximal depression.
[3]Dose (μg/kg) to reverse amphetamine by 50%.
[4]Maximal reversal.
i.a. = inactive
n.t. = not tested

TABLE 4

BEHAVIORAL EFFECTS OF 1-[4-[4-(2-METHOXYPHENYL)-1-PIPERAZINYL]BUTYL]-3-PHENYL-2-IMIDAZOLIDINONE AND HALOPERIDOL[1]

| | Antagonism Amphetamine | |
|---|---|---|
| | Stereotypy | Catalepsy[2] |
| Haloperidol | 1.0 | 1.0 |
| 1-[4-[4-(2-methoxyphenyl)-1-piperazinyl]butyl]-3-phenyl-2-imidazolidinone (Example 1) | 0.3 | 10 |

[1]Threshold dose for effect (mg/kg).
[2]Defined as 200% increase in time a rat will spend leaning on a box without aid.

We claim:

1. A compound of Formula I

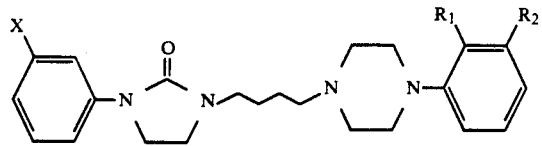

wherein
X is hydrogen or Cl;
$R_1$ and $R_2$ are the same or different and are selected from the group consisting of hydrogen, methoxy, and ethoxy, provided that only one of $R_1$ or $R_2$ is hydrogen; or a pharmacologically acceptable salt thereof.

2. A compound according to claim 1, wherein X is hydrogen.

3. A compound according to claim 1, wherein X is Cl.

4. A compound according to claim 2, selected from the group consisting of
1-[4-[4-(2-methoxyphenyl)-1-piperazinyl]butyl]-3-phenyl-2-imidazolidinone,
1-[4-[4-(2-ethoxyphenyl)-1-piperazinyl]butyl]-3-phenyl-2-imidazolidinone,
1-[4-[4-(3-methoxyphenyl)-1-piperazinyl]butyl]-3-phenyl-2-imidazolidinone, and
1-[4-[4-(3-ethoxyphenyl)-1-piperazinyl]butyl]-3-phenyl-2-imidazolidinone.

5. A compound according to claim 4, which is 1-[4-[4-(2-methoxyphenyl)-1-piperazinyl]butyl]-3-phenyl-2-imidazolidinone.

6. A compound according to claim 3, selected from the group consisting of
1-(3-chlorophenyl)-3-[4-[4-(2-methoxyphenyl)-1-piperazinyl]butyl]-2-imidazolidinone,
1-(3-chlorophenyl)-3-[4-[4-(2-ethoxyphenyl)-1-piperazinyl]butyl-2-imidazolidinone,
1-(3-chlorophenyl)-3-[4-[4-(3-methoxyphenyl)-1-piperazinyl]butyl-]2-imidazolidinone, and
1-(3-chlorophenyl)-3-[4-[4-(3-ethoxyphenyl)-1-piperazinyl]butyl]-2-imidazolidinone.

7. A compound according to claim 6, which is 1-(3-chlorophenyl)-3-[4-[4-(2-methoxyphenyl)-1-piperazinyl]butyl]-2-imidazolidinone.

8. A method of treating schizophrenia by administering an effective amount of a compound of Formula I according to claim 1 to a human patient.

9. The method according to claim 8 wherein the compound is 1-[4-[4-(2-methoxyphenyl)-1-piperazinyl]butyl]-3-phenyl-2-imidazolidinone.

10. The method according to claim 8 wherein the compound is 1-(3-chlorophenyl)-3-[4-[4-(2-methoxyphenyl)-1-piperazinyl]butyl]-2-imidazolidinone.

11. A method of treating Parkinsonism by administering an effective amount of a compound of Formula I according to claim 1 to a human patient.

12. The method according to claim 11 wherein the compound is 1-[4-[4-(2-methoxyphenyl)-1-piperazinyl]butyl]-3-phenyl-2-imidazolidinone.

13. The method according to claim 11 wherein the compound is 1-(3-chlorophenyl)-3-[4-[4-(2-methoxyphenyl)-1-piperazinyl]butyl]-2-imidazolidinone.

* * * * *

UNITED STATES PATENT AND TRADEMARK OFFICE
CERTIFICATE OF CORRECTION

PATENT NO. : 5,281,594
DATED : Jan. 25, 1994
INVENTOR(S) : Montford F. Piercey, et al It is certified that error appears in the above-indentified patent and that said Letters Patent is hereby corrected as shown below:

| Patent Reads: | Should read: |
|---|---|
| On title page, item [54] "ONS AND ANTIHYPERTENSIVE" | -- CNS AND ANTIHYPERTENSIVE -- |
| At column 1, line 3, "WITH ONS" | -- WITH CNS -- |
| At column 2, line 58, "generally" | -- generically -- |
| At column 3, line 10, "10-octahydrobenzo " | -- 10b-octahydrobenzo -- |
| At column 4, line 33, "base." | -- abuse. -- |
| At column 6, line 9, "(1-3-chlorophenyl " | -- (1-(3-chlorophenyl -- |
| At column 11, line 21, no title is shown for Table 3. | -- EFFECTS OF DOPAMINERGIC AGENTS ON DOPAMINE NERVE IMPULSE GENERATION -- |
| At column 11, line 37, "SDZ 209-912" | -- SDZ 208-912 -- |

Signed and Sealed this

Twenty-fourth Day of May, 1994

BRUCE LEHMAN

*Attest:*

*Attesting Officer*    *Commissioner of Patents and Trademarks*